United States Patent [19]

Cornett, III

[11] 4,411,656
[45] Oct. 25, 1983

[54] COMPRESSIBLE SYRINGE

[75] Inventor: Walter G. Cornett, III, Wheeling, Ill.

[73] Assignee: Urologic & Enteric Research Associates, Wheeling, Ill.

[21] Appl. No.: 343,886

[22] Filed: Jan. 29, 1982

[51] Int. Cl.³ .............................................. A61M 1/00
[52] U.S. Cl. .................................... 604/212; 604/263
[58] Field of Search ..................... 128/216, 215, 218 P, 128/218 PA, 218 N, 232; 604/212, 187, 263

[56] References Cited

U.S. PATENT DOCUMENTS

| 2,699,167 | 1/1955 | Raiche | 128/216 |
| 2,717,598 | 9/1955 | Krasno | 128/216 |
| 2,731,053 | 1/1956 | Lockhart | 128/216 X |
| 2,935,067 | 5/1960 | Bouet | 128/216 |
| 4,007,740 | 2/1977 | Owen | 128/218 N |

FOREIGN PATENT DOCUMENTS 1511044 1/1968 France ............................. 128/216

Primary Examiner—John D. Yasko
Attorney, Agent, or Firm—Robert E. Wagner; Alan L. Barry

[57] ABSTRACT

An improved one-piece disposable fluid-filled compressible syringe comprised of a shielding disc molded into a substantially intermediate portion of the syringe neck and lying perpendicular to the longitudinal axis of the syringe to promote aseptic technique in manipulating the syringe during use. The syringe also includes an improved syringe cap comprised of a disc, perpendicularly oriented to the longitudinal axis of the syringe, a semi-circular gripping piece perpendicularly mounted to one surface of the disc and a sleeve to receive the syringe tip mounted to the disc surface opposite to the surface to which the gripping piece is attached. The disc included in the syringe cap prevents a user's fingers from contacting the syringe tip during removal or replacement of the cap.

8 Claims, 6 Drawing Figures

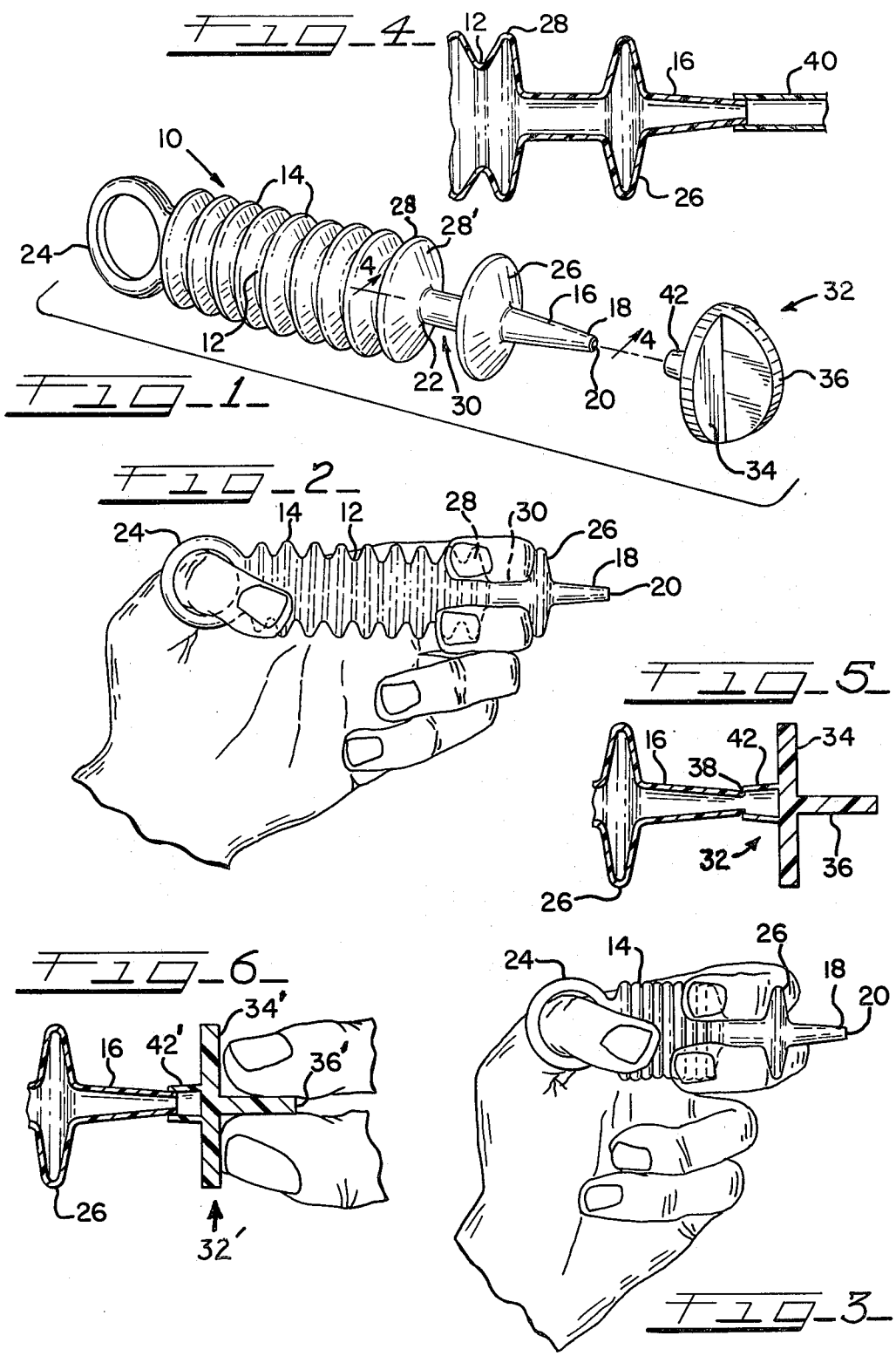

COMPRESSIBLE SYRINGE

DESCRIPTION

Technical Field

The present invention generally relates to disposable instruments for use in the medical and scientific fields and, more specifically, to an improved, fluid-filled compressible syringe for aseptically performing irrigations, and for injecting or dispensing drugs, lubricating jellies and other fluids or solutions.

Background of the Invention

Syringes for general use in medical and scientific procedures are now manufactured having a syringe body which can be entirely compressed to eject the contents contained in lieu of the cylinder and piston arrangement of prior art syringes. Compressible syringes are now prefilled during their manufacture with sterile water, saline, isotonic solutions or other fluids. Such prefilled syringes have found wide spread use and application throughout the medical industry particularily syringes of 10 cc and 30 cc volume which are useful in inflating Foley catheters, in dispensing lubricating jellies and in dispensing drugs into solutions for intravenous introduction into a patient or by other parenteral methods. Several examples of these syringes are disclosed in Boucher, U.S. Pat. No. 3,938,514; Bane, U.S. Pat. No. 3,340,869; and Elinger, U.S. Pat. No. 2,911,972.

In using any syringe, it is essential to follow proper aseptic technique and procedure. A primary objective of such technique is to maintain the sterile field about the tip of the syringe. If this aseptic field is invaded by either the user's fingers or other objects, contamination of the syringe tip will result, with the possibility of exposing a patient to infection. One cause of contamination of the syringe tip in compressible syringes commonly occurs during removal of the protective cap from the tip of the syringe. Prior art syringe caps generally are sleeves which are tightly fitted to the syringe tip and provide no adequate means to facilitate removal or replacement of the cap. Hence, a user's finger tips will protrude over and around the edges of the syringe cap so that during its removal, the user's finger tips may come into contact with the syringe tip.

Another cause of contamination of the syringe tip occurs through the handling of the syringe during its use. Generally, a user will grasp a syringe in one hand, placing the portion of the syringe body closest to the syringe tip between his forefinger and middle finger, while the thumb of the same hand rests on the end of the syringe opposite the syringe tip. This manipulation of the syringe body allows a user to compress the syringe body, causing the fluid contained to be expelled. Although some prior art syringes employ annular fingerpieces or gripping prongs to assist in a user's handling of the syringe, such devices do not insure that a user will follow aseptic procedures. That is, prior art syringes could be used without having to utilize the gripping prongs or similar structures provided on the syringe body. Hence, a substantial risk exists that a user's fingers could slip downward to come in contact with the syringe tip causing contamination of the tip.

A syringe tip also can become contaminated by contacting objects after the syringe cap has been removed. This usually occurs as a result of a user placing a syringe on a table-top or propping the syringe against an object after the syringe cap has been removed. Neither prior part syringes nor syringe caps have been designed to provide a means for minimizing contact of an exposed syringe tip with surrounding objects.

SUMMARY OF THE INVENTION

In accordance with the present invention, a fluid-filled compressible syringe has been developed which minimizes the risk of contamination of the syringe tip during both removal of the syringe cap and while the syringe is being manipulated during use. The present invention maintains the aseptic field about the syringe tip through an improved syringe design which utilizes three protective barriers which preferrably are discs. Since the present invention is manufactured by the blow-molding of pliable plastics such as polypropylene, polyethylene or surgical grade polyvinyl chloride, the protective discs may be molded into the syringe during its manufacture. One protective disc is molded within the terminal portion of the compressible body to which the neck is attached while another protective disc is incorporated into an intermediate portion of the syringe neck. The third protective disc forms part of a protection cap which fits over the tip of the syringe.

Specifically, the present invention is a fluid-filled compressible syringe of the type having a hollow compressible body for containing fluid and a hollow tapered neck attached to a terminal portion of the body through which fluid is conducted. The syringe body is made compressible by a series of bellow structures extending the length of the body which contract when a user squeezes the syringe causing the contained fluid to be expelled. The preferred form of the present invention improves upon existing compressible syringe design by incorporating a first disc, having a hollow interior, into the syringe body so that one surface of the disc is contiguous with the body and the other disc surface is perpendicular to the longitudinal axis of the syringe. The first disc is molded into the same end of the syringe body to which the neck is attached so that the neck extends through the center of the disc. A second hollow disc is molded at a substantially intermediate portion of the syringe neck so that both surfaces of the second disc lie perpendicular to the longitudinal axis of the syringe. The neck protrudes through the center of one surface of the second disc and exits from the center of the other surface of the second disc. It is to be noted that the hollow interiors of the first and second disc are in direct communication with the interior of the neck and syringe body which is a result of the blow-molding technique employed in manufacturing the present invention.

Further, at the end of the syringe body, opposite to the end to which the neck is attached, an annular piece is provided to receive the thumb of the user to assist in the compression of the syringe body.

The present invention further includes a cap which preferably is incorporated into the syringe tip. The cap is comprised of a solid disc oriented so that the surface of the disc lies perpendicular to the longitudinal axis of the syringe, a gripping piece which is perpendicularly mounted to the surface of the disc to function as a handle to facilitate removal of the cap and a tapered sleeve mounted to the surface of the solid disc opposite to the gripping piece which is blow-molded as an integral part of the syringe tip. The cap is removed from the syringe tip by breaking it off from the tip along a scored line circumscribed around the circumference of the syringe tip. The gripping piece and the protective disc of the cap are perpendicular to each other to shield the tip by preventing the user's fingers from contacting the syringe tip during removal of the cap.

BRIEF DESCRIPTION OF THE DRAWINGS

FIG. 1 is an exploded view perspective of the present invention illustrating the protective cap having been removed from the syringe tip;

FIG. 2 illustrates the method by which the invention is gripped by a user;

FIG. 3 illustrates a user compressing the collapsable body of the present invention to expel fluid therein contained;

FIG. 4 is a detailed vertical section viewed along line 4—4 of FIG. 1 illustrating the insertion of the neck of the present invention into an open end of surgical tubing;

FIG. 5 is a view similar to that of FIG. 4 illustrating the preferred embodiment of a cap incorporated into the syringe tip; and, FIG. 6 is the same view as FIG. 5 illustrating another embodiment of a protective syringe cap which fits over the syringe tip and can be removed and replaced onto the syringe tip.

DETAILED DESCRIPTION

Referring now to the drawings, FIG. 1 discloses a compressible syringe generally referenced by 10. Syringe 10 is comprised of a hollow body 12 which is made compressible by bellow structures 14 which extend the entire length of body 12. Attached to a terminal portion of body 12 is neck 16 which gradually tapers inward to form a syringe tip 18 and orifice 20 through which fluid expelled from syringe body 12 is conducted. It is contemplated that syringe tip 18 may be modified to receive a Luer tip to engage an injection needle thus convering syringe 10 to a hypodermic surgical syringe. Neck 16 is attached to syringe body 12 at such point 22, so that the interior of syringe 12 is in direct communication with the interior of neck 16. Molded at the end of syringe body 12, opposite to neck 16, is an annular thumb piece 24 for receiving the thumb of a user during the handling and manipulation of syringe 10. Although the preferred form of the invention discloses thumb piece 24 as a ring-shaped structure, it is contemplated that any suitable means for engaging the user's thumb to facilitate compression of the syringe body is satisfactory.

FIG. 1 further discloses a platform molded into a substantially intermediate portion of neck 16 which in the preferred form of the invention, is a hollow disc 26 incorporated into neck 16 so that both surfaces of disc 26 are perpendicular to the longitudinal axis of the syringe 10. Though neck 16 enters disc 26 at the center of one disc surface and leaves from the center of the other disc surface, the interior of disc 26 is in direct communication with interior neck 16. Disc 26 functions as a shield or a barrier to prevent the fingers of a user from sliding forward to contact syringe tip 18, minimizing the risk that syringe tip 18 may become contaminated by improper handling of syringe 10. Although disc 26 has a hollow interior, it is conceivable that disc 26 may be a solid platform or shield or any shape which acts as a barrier to prevent a user's fingers from coming in contact with syringe tip 18. Disc 26 also functions to support and balance syringe 10 so that when a user places a syringe with an exposed tip 18 on a level surface, syringe tip 18 is elevated above the surface thus preventing syringe tip from contacting the surface itself.

Syringe 10 further includes a disc 28 formed within the terminal portion of syringe body 12 to which neck 16 is attached at point 22. Disc 28 is oriented so that one disc surface 28' is perpendicular to the longitudinal axis of syringe 10 while the opposing surface of disc 28 is contiguous with body 12. The hollow interior of disc 28 is in direct communication with the interior of body 12 and neck 16. As disc 26 and 28 are parallel to each other a space is formed between them along neck 16 to provide a gripping region 30 for a user's fingers. Gripping region 30 assists in the use of the syringe and defines a user's fingers to maintain the aseptic field about syringe tip 18.

FIG. 1 also illustrates a syringe cap 32 comprised of a disc 34. Mounted to one surface of disc 34 is a semicircular gripping piece 36 and mounted to the opposing surface of disc 34 is a sleeve 42 which in the preferred form of cap 32 is blow-molded as an integral part of neck 16. Disc 34 functions in the same manner as disc 26 in that disc 34 prevents a user's fingers from contacting the contaminating syringe tip 18 during removal of syringe cap 32.

FIG. 2 illustrates a method of using the preferred form of the present invention in which a user's forefinger and middle finger are inserted into gripping region 30 and wrap around disc 28. Because of disc 26 the movement of a user's forefinger and middle finger will be confined to gripping region 30 during use of the syringe 10. The positioning of disc 26 along neck 16 insures that proper aseptic technique will be followed in using syringe 10 since the only effective method of compressing body 12 is by a user gripping syringe 10 behind disc 26. That is, in order to apply force against disc 28 to effect a complete compression of body 12, a user's fingers must necessarily remain behind disc 26. Hence, unlike prior art syringes, it is nearly impossible for a user to engage in sloppy aseptic technique since the present invention can only be effectively operated by a method which promotes proper handling of the syringe thus maintaining the aseptic region about syringe tip 18. Although it is conceivable that a user may use two hands in attempting to effect the contraction of body 12, a user's fingers will still have to be positioned behind disc 26 in order to apply the requisite pressure against disc 28 to cause such contraction.

FIG. 3 illustrates the contraction mode of body 12 causing the fluid contained within body 12 to be expelled through orifice 18. It is to be noted that in the contraction mode a user's fingers still remain positioned behind disc 26, thus maintaining the sterility of syringe tip 18.

FIG. 4 discloses in cross section, the insertion of syringe tip 18 into a receiving end of tubing 40. This procedure commonly occurs during the inflation of a retaining catheter. FIG. 4 also illustrates that in the preferred form of the invention hollow interiors of body 12, disc 26 and 30 and neck 16 all are in direct communication with each other so that when fluid is expelled from body 12 it fills the interior chambers of neck 16 and discs 26 and 28. This feature is a consequence of the blow-molding manufacture of syringe 10. Blow-molding of syringe 10 from a pliable plastic creates a one-piece instrument which is light-weight, but still possesses the structural detain necessary to the performance of the syringe.

FIG. 5 illustrates a preferred syringe cap 32 which when manufactured through blow-molding forms an integral part of neck 16. Syringe cap 32 is comprised of a platform 34 and a gripping piece 36 which is perpendicularly mounted to one face of platform 34. Cap 32 further includes a sleeve 42 mounted to an opposing face of platform 34. Sleeve 42 comprises a part of neck 16 so that sleeve 42, and therefore cap 32, is an extension of neck 16.

In utilizing cap 32, a user grips gripping piece 36 with his thumb and forefinger and snaps cap 32 off of tip 18 along a circumferential notch 38 which is scored into the walls of neck 16 about the circumference of neck 16. Notch 38 provides a sterile means of neatly removing cap 32 to expose orifice 20 of syringe tip 18. Since it is contemplated that syringe 10 will be pre-filled with a selected sterile fluid during manufacture, notch 38 also provides a leak-proof seal to permit syringe 10 to effectively function as a fluid container until removal of cap 32.

Further, platform 34 of cap 32 could be any shape so long as it prevents a user's fingers from extending over and around the syringe cap thus decreasing the possibility of a user's fingers coming in contact with syringe tip 18. Prior art syringe caps are generally elongated sleeves which fit over a syringe tip and provide neither an adequate gripping surface nor sufficient clearance between the cap and tip with which to remove the cap. Thus when a user attempts to remove a prior art syringe cap, a user's fingers would often contact the syringe tip. Cap 32 improves upon prior art design by including gripping piece 36 which preferrably has a semi-circular shape, perpendicularly mounted to platform 34 to provide a gripping handle to prevent contact with sleeve 42.

Finally, FIG. 6 illustrates another embodiment of the syringe cap of the present invention generally referenced by 32'. Syringe cap 32' includes many of the same elements as cap 32, namely a platform 34', a gripping piece 36' and a sleeve 42'. However, sleeve 42' is made to receive the tip of neck 16 to permit cap 32' to be removed and easily replaced onto neck 16.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the invention, but that the invention will include all embodiments falling within the scope of the appended claims.

I claim:

1. In a syringe of the type having a hollow body made compressible by bellow structures and a tubular neck wherein one end of the neck is axially mounted to a terminal portion of the body and the other end of the neck tapers inward to form a tip having an opening through which fluid may pass upon compression of the body, the improvement comprising:
    a first hollow platform molded into said terminal portion and perpendicular to the longitudinal axis of the syringe so that said neck protrudes from the center of one side of said first platform while the other side of said platform is contiguous with said body, such that the interiors of said body and said first platform are in communication with each other; and
    a second hollow platform molded into an intermediate portion of said neck and perpendicular to the longitudinal axis of the syringe and parallel to said first platform so that said neck centrally enters one surface of said second platform and centrally exits from the opposing surface of said second platform so that the interiors of said neck and said second platform are in direct communication with each other and a space is formed between said first and second platforms to provide a gripping region for a user's fingers during operation of the syringe.

2. The syringe described in claim 1 further including means for covering the tip comprising:
    a platform perpendicular to the longitudinal axis of the syringe;
    a gripping member which is perpendicularly mounted to said third platform and
    a sleeve molded to the tip and mounted on the opposite surface of said platform such that when a user grasps said gripping means to remove said covering means, said platform prevents the user's fingers from contacting the tip.

3. The syringe described in claim 2, wherein said platform is circular and said gripping member is semi-circular such that the linear peripheral edge of said semi-circular member is mounted to the surface of said circular platform.

4. The syringe described in claim 1 further comprising:
    a pressure application means attached to a terminal portion of said body opposite from said terminal portion to which said neck is attached to receive a user's thumb in compressing said body.

5. The syringe described in claim 4, wherein said pressure application means includes a ring.

6. A cap for covering the tip of a syringe having a compressible body comprising:
    a shielding platform perpendicularly oriented to the longitudinal axis of the syringe body, said platform having surface area dimensions substantially equivalent to the cross-sectional dimensions of the syringe body;
    a semi-circular gripping tab perpendicularly mounted to one surface of said platform; and
    a tapered sleeve to receive the syringe tip, said sleeve mounted to the surface of said platform opposite from the surface to which said tab is mounted, so that when a user grasps said tab to remove or replace said cap the surface area dimensions of said platform shields a user's fingers from contacting any portion of the syringe tip.

7. The syringe described in claim 2 wherein said cap may be removed by snapping said sleeve off the tip of the syringe along a circumferential notch scored into the neck and about the circumference of the neck.

8. In a syringe of the type having a hollow body made compressible by bellow structures and a tubular neck wherein one end of the neck is axially mounted to a terminal portion of the body and the other end of the neck tapers inward to form a tip having an opening through which fluid may pass upon compression of the body, the improvement comprising:
    at least one shielding platform molded into said neck, said platform being perpendicular to the longitudinal axis of the syringe so that said neck protrudes through said platform, such that said platform acts as an aseptic barrier to prevent a user's fingers from contacting said tip.

* * * * *